United States Patent [19]

Gregory

[11] Patent Number: 5,571,151
[45] Date of Patent: Nov. 5, 1996

[54] METHOD FOR CONTEMPORANEOUS APPLICATION OF LASER ENERGY AND LOCALIZED PHARMACOLOGIC THERAPY

[76] Inventor: Kenton W. Gregory, 9205 SW. Barnes Rd., Portland, Oreg. 97225

[21] Appl. No.: 328,857

[22] Filed: Oct. 25, 1994

[51] Int. Cl.$^6$ .................................................. A61B 17/32
[52] U.S. Cl. .................................. 607/88; 606/15; 606/7; 604/20
[58] Field of Search ................ 607/88–90; 604/20, 604/21; 606/7, 8, 10, 13–16, 17

[56] References Cited

U.S. PATENT DOCUMENTS

| | | |
|---|---|---|
| 3,858,577 | 1/1975 | Bass et al. . |
| 3,995,934 | 12/1976 | Nath . |
| 4,011,403 | 3/1977 | Epstein et al. . |
| 4,045,119 | 8/1977 | Eastgate . |
| 4,201,446 | 5/1980 | Geddes et al. . |
| 4,313,431 | 2/1982 | Frank . |
| 4,445,892 | 5/1984 | Hussein et al. ............................. 606/7 |
| 4,641,912 | 2/1987 | Goldenberg . |
| 4,697,870 | 10/1987 | Richards . |
| 4,848,336 | 7/1989 | Fox et al. . |
| 4,875,897 | 10/1989 | Lee ............................................. 606/7 |
| 4,927,231 | 5/1990 | Levatter . |
| 4,976,710 | 12/1990 | Mackin ..................................... 607/88 |
| 5,053,033 | 10/1991 | Clarke ...................................... 607/89 |
| 5,169,396 | 12/1992 | Dowlatshahi et al. ..................... 607/89 |
| 5,187,572 | 2/1993 | Nakamura et al. . |
| 5,188,632 | 2/1993 | Goldenberg . |
| 5,217,454 | 6/1993 | Khoury . |
| 5,246,437 | 9/1993 | Abela ....................................... 604/20 |
| 5,304,171 | 4/1994 | Gregory et al. . |

FOREIGN PATENT DOCUMENTS 87304072.9  12/1987  European Pat. Off. .

OTHER PUBLICATIONS

Gregory, Kenton W. and Anderson, R. Rox, "Light Core Light Guide for Laser Angioplasty," IEEE Journal of Quantum Electronics, vol. 26, No. 12, pp. 2289–2296, Dec. 1990.

*Primary Examiner*—Angela D. Sykes
*Assistant Examiner*—Robert L. Nasser, Jr.
*Attorney, Agent, or Firm*—Marger, Johnson, McCollom & Stolowitz, P.C.

[57] ABSTRACT

A method for contemporaneously applying laser energy and locally delivering pharmacologic therapy to a selected site in a body lumen using a liquid core laser angioscope catheter. The method comprises preparing a solution of a pharmacologic agent, inserting the catheter into the lumen, directing the catheter to the site, transmitting visible light to the site, flowing the light transmissive liquid through the catheter, viewing the site, transmitting laser energy through the liquid filled catheter to treat the site, and introducing a flow of the pharmacologic agent in solution into the catheter for contemporaneous discharge at the distal end into the lumen adjacent the site.

12 Claims, 2 Drawing Sheets

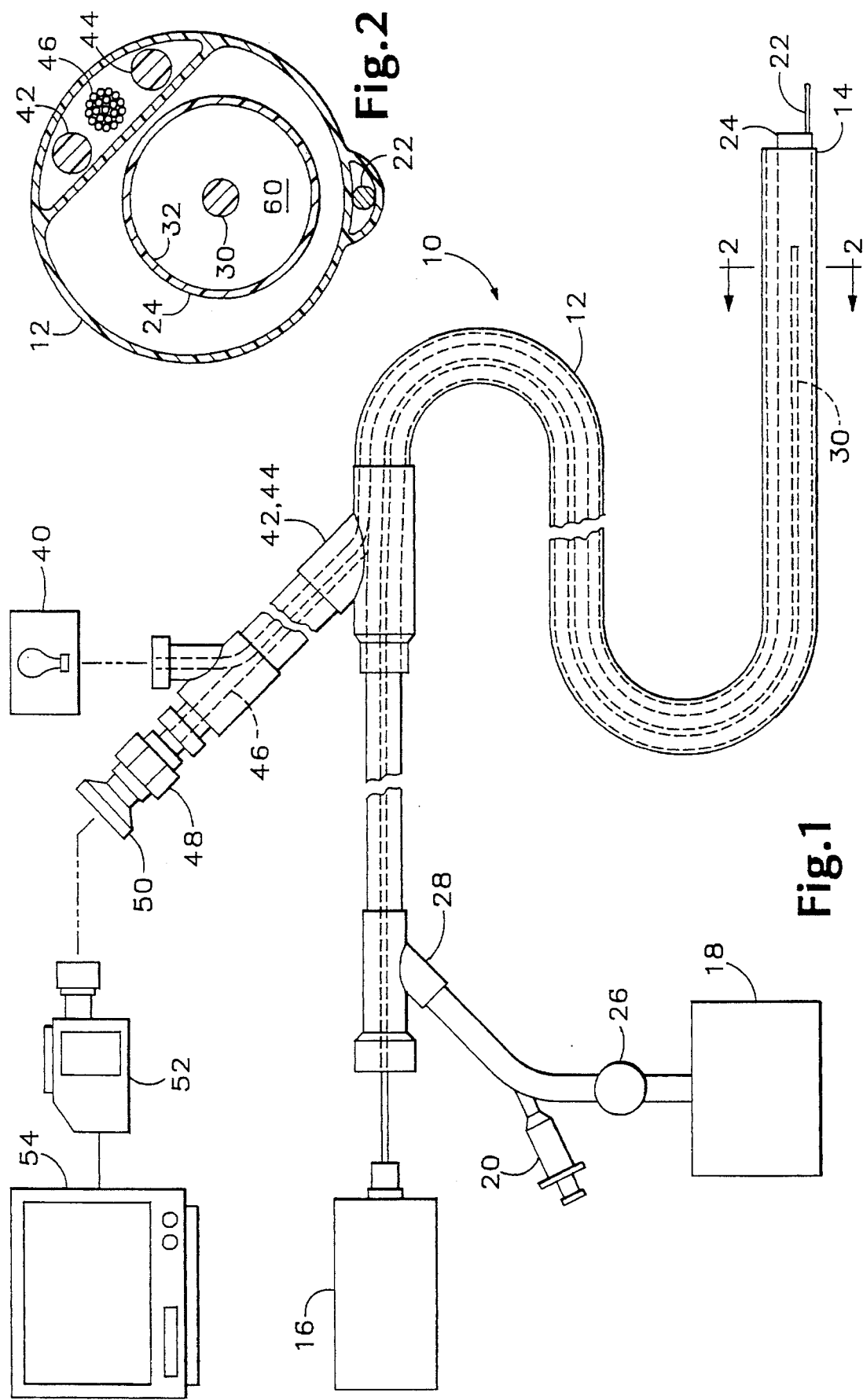

METHOD FOR CONTEMPORANEOUS APPLICATION OF LASER ENERGY AND LOCALIZED PHARMACOLOGIC THERAPY

BACKGROUND OF THE INVENTION

1. Field of the Invention

The present invention relates to a method and apparatus for contemporaneous application of laser energy and localized delivery of pharmacologic therapy to a site within a body lumen. More specific applications of the present invention relate to a method and apparatus for localized treating of vascular thrombosis disorders, atherosclerosis, and tumors.

2. Description of Prior Art

Atherosclerosis, which is a major cause of cardiovascular disease, resulting in heart attacks, is characterized by the progressive accumulation of atherosclerotic deposits (known as plaque) on the inner walls of the arteries. As a result, blood flow is restricted and there is an increased likelihood of clot formation that can partially or completely block or occlude an artery, causing a heart attack. Arteries narrowed by atherosclerosis that cannot be treated effectively by drug therapy are typically treated by medical procedures designed to increase blood flow, including highly invasive procedures such as coronary artery bypass surgery and less invasive procedures such as balloon angioplasty, atherectomy and laser angioplasty.

Bypass surgery involves opening the patient's chest and transferring a vein cut from the patient's leg to the heart to construct a detour around the occluded artery. Bypass surgery requires prolonged hospitalization and an extensive recuperation period. Furthermore, bypass surgery also exposes the patient to a risk of major surgical complications. Balloon angioplasty is a less invasive and less costly alternative to bypass surgery and is performed in a hospital cardiac catheterization laboratory by an interventional cardiologist. In this procedure, a balloon-tipped catheter is inserted into a blood vessel through a small incision in the patient's arm or leg. The physician uses a guide catheter to feed the balloon through the patient's blood vessels to the occluded artery. At that point, a guidewire is inserted across the deposits of atherosclerotic plaque, known as lesions, to provide a pathway for the balloon catheter. The deflated balloon is advanced over the guidewire, positioned within the occluded area and inflated and deflated several times. This inflation and deflation usually tears the plaque and expands the artery beyond its point of elastic recoil. Thus, although no plaque is removed, the opening through which blood flows is enlarged.

Atherectomy employs a rotating mechanical device mounted on a catheter to cut and remove plaque from a diseased artery. Although atherectomy, unlike balloon angioplasty, removes plaque from coronary arteries, existing atherectomy devices are not effective in treating certain types of lesions.

Laser angioplasty removes plaques by using light, in varying wavelengths ranging from ultraviolet to infrared, that is delivered to the lesion by a fiber optic catheter. Early attempts to develop a laser angioplasty system used continuous wave thermal lasers that generated heat to vaporize plaque. These laser systems caused charring and significant thermal damage to healthy tissue surrounding the lesion. As a result, thermal laser systems have generally been regarded as inappropriate for use in the coronary arteries. In contrast, excimer lasers use ultraviolet light to break the molecular bonds of atherosclerotic plaque, a process known as photoablation. Excimer lasers use electric, ally excited xenon and chloride gases to generate an ultraviolet laser pulse with a wavelength of 308 nanometers. This wavelength of ultraviolet light is absorbed by the proteins and lipids that comprise plaque, resulting in precise ablation of plaque and the restoration of blood flow without significant thermal damage to surrounding tissue. The ablated plaque is converted into carbon dioxide and other gases and minute particulate matter that can be easily eliminated.

In laser angioplasty, conventional light guides using fiber optics are used to direct laser energy onto arterial plaque formations to ablate the plaque or thrombus and remove the occlusion. Individual optically conducting fibers are typically made of fused silica or quartz, and are generally fairly inflexible unless they are very thin. A thin fiber flexible enough to pass through a lumen halving curves of small radius, such as through arterial lumens from the femoral or the brachial artery to a coronary artery, typically projects a beam of laser energy of very small effective diameter, capable of producing only a very small opening in the occlusion. Moreover, the energy is attenuated over relatively small distances as it passes within a thin fiber. Small diameter fibers can mechanically perforate vessels when directed against the vessel wall as they are passed within the vessel toward the site.

In order to bring a sufficient quantity of energy from the laser to the thrombus or plaque, light guides proposed for use in laser angioplasty usually include a number of very thin fibers, each typically about 50 to 200 microns in diameter, bundled together or bound in a tubular matrix about a central lumen, forming a catheter. Laser energy emerging from a small number of fibers bundled together produces lumens of suboptimal diameter which can require subsequent enlargement by, for example, balloon dilation. Such devices do not always remove an adequate quantity of matter from the lesion, and their uses are generally limited to providing access for subsequent conventional balloon angioplasty.

Although individual fibers of such small dimensions are flexible enough to negotiate curves of fairly small radius, a bundle of even a few such fibers is less flexible and more costly. Coupling mechanisms for directing laser energy from the source into the individual fibers in a light guide made up of multiple small fibers can be complex. Improper launch of the laser energy into such a light guide can destroy the fibers. The directing of laser energy into arteries or veins thus far has been limited to two-dimensional imaging with fluoroscopy. Frequently, it is not possible to distinguish whether the laser catheter is contacting plaque, normal tissue, or thrombus—all of which have very different therapeutic consequences as well as possible adverse side effects.

An alternative to conventional optical fiber technology using fused silica fibers or fiber bundles, is the use of fluid core light guides to transmit light into the body, as discussed by Gregory et al. in the article "Liquid Core Light Guide for Laser Angioplasty", *IEEE Journal of Quantum Electronics*, Vol. 26, No. 12, December 1990, incorporated herein. While fluid-core light guides may offer improvements of fused silica fibers or bundles, initial animal and clinical studies indicate inadequate or only partial removal of thrombus or athlerosclerotic material, and a recurrence of athlerosclerosis after treatment.

Another approach to treating atherosclerosis orthrombosis is to degrade thrombi and plaque by treatment with various pharmacologic agents. Many techniques currently exist for delivering medicant and other active agents to body tissue. These include: oral administration, direct injection into body tissue, and intravenous administration which involves introducing the active agent directly into the blood stream. These delivery mechanisms are systemic, in that they deliver the active agent via the bloodstream throughout the entire body. Effective pharmacologic or drug therapy requires achieving adequate concentrations of an active drug at the site of desired treatment without producing concentrations of the drug elsewhere in the body that create unwanted or dangerous side effects.

Workers in the field have discovered that many effective drugs which are capable of treating or curing disease cannot be effectively delivered systemically because the concentrations necessary for effective treatment produce adverse side effects in other parts of the body. For example, in the case of arterial and venous thrombosis, workers in the field have identified many potent agents which are capable of degrading thrombi, but clinical application of these agents has been limited by bleeding complications which can result in substantially increased morbidity and mortality. Moreover, even clinically approved agents such as streptokinase, urokinase, recombinant tissue plasminogen activators or even heparin have limited efficacy in treating acute myocardial infarction and other thrombotic disorders because they can produce systemic bleeding complications.

One approach to reducing systemic side effects is to introduce a catheter percutaneously, through the skin, near the thrombotic site under fluoroscopic guidance. The active agent is then infused in high concentrations and flowed by the thrombus. There are, however, practical limits to the duration of such treatment. Prolonged infusion will eventually produce a total accumulated systemic dose of the agent sufficient to create adverse side effects. Enzymatic degradation is in large part dependent upon the surface area of the thrombus which is exposed to the enzyme—which is limited to current infusion of enzymes which flow by the thrombus. In addition to the great cost of such an infusion, the prolonged indwelling of the catheter increases morbidity. The ability to administer an active agent locally to the thrombotic site without systemically affecting other tissues or creating complications, would greatly enhance the ability to effectively treat arterial and venous thrombus.

Another application for delivering an active agent to an internal body tissue is in treating cancerous tumors. The objective of such treatment is to concentrate as much of the cancer drug or gene product in the tumor as possible. Typically, workers in the field administer cancer drugs systemically through the blood stream and then use various means to localize the drug in the cancerous tumor. Nevertheless, amounts of the drug still circulate through the blood stream in sufficient concentrations to produce adverse side effects and therefore limit the dosages of the drug which can be safely administered.

Accordingly, a need remains for a method and apparatus for locally delivering an active agent in conjunction with delivering laser energy to internal body tissue. There is a further need for such an apparatus and method for treating atherosclerosis, thrombosis, cancerous tumors, and other internal body tissue.

SUMMARY OF THE INVENTION

The invention provides a method for contemporaneously applying laser energy and locally delivering pharmacologic therapy to a selected site in a body lumen using a liquid core laser catheter. The catheter includes a flexible tube having a distal end for insertion into the lumen, a conduit housed within the tube, means for coupling a flow of light transmissive liquid from an external source into the conduit, means for transmitting laser energy from an energy source into the conduit, the conduit having a sidewall capable of internally reflecting light into the liquid in the conduit so that the liquid waveguides the laser energy through the conduit to the site. The method comprises the steps of preparing a dose of pharmacologic agent, introducing the dose of pharmacologic agent into the light transmissive liquid, inserting the catheter into the lumen, directing the catheter to the site, flowing the light transmissive liquid, containing the pharmacologic agent, through the conduit for discharge at the distal end into the lumen adjacent the site contemporaneously with light or laser energy delivery via the light transmissive liquid. The term "contemporaneously" means during or proximately before or after, as applicable to the treatment.

Using a liquid core laser catheter for treatment of thrombosis or athlerosclerosis can thereby be augmented by the additional administration of high-dose pharmacologic therapies at the site contemporaneous with the discharge of light energy from the catheter to help remove residual thrombus or prevent recurrence of thrombosis or athlerosclerosis.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 1 is a schematic diagram of a liquid core laser drug delivery system according to the present invention.

FIG. 2 is a cross-sectional view taken along lines 2—2 of FIG. 1.

DETAILED DESCRIPTION

Figure 3:
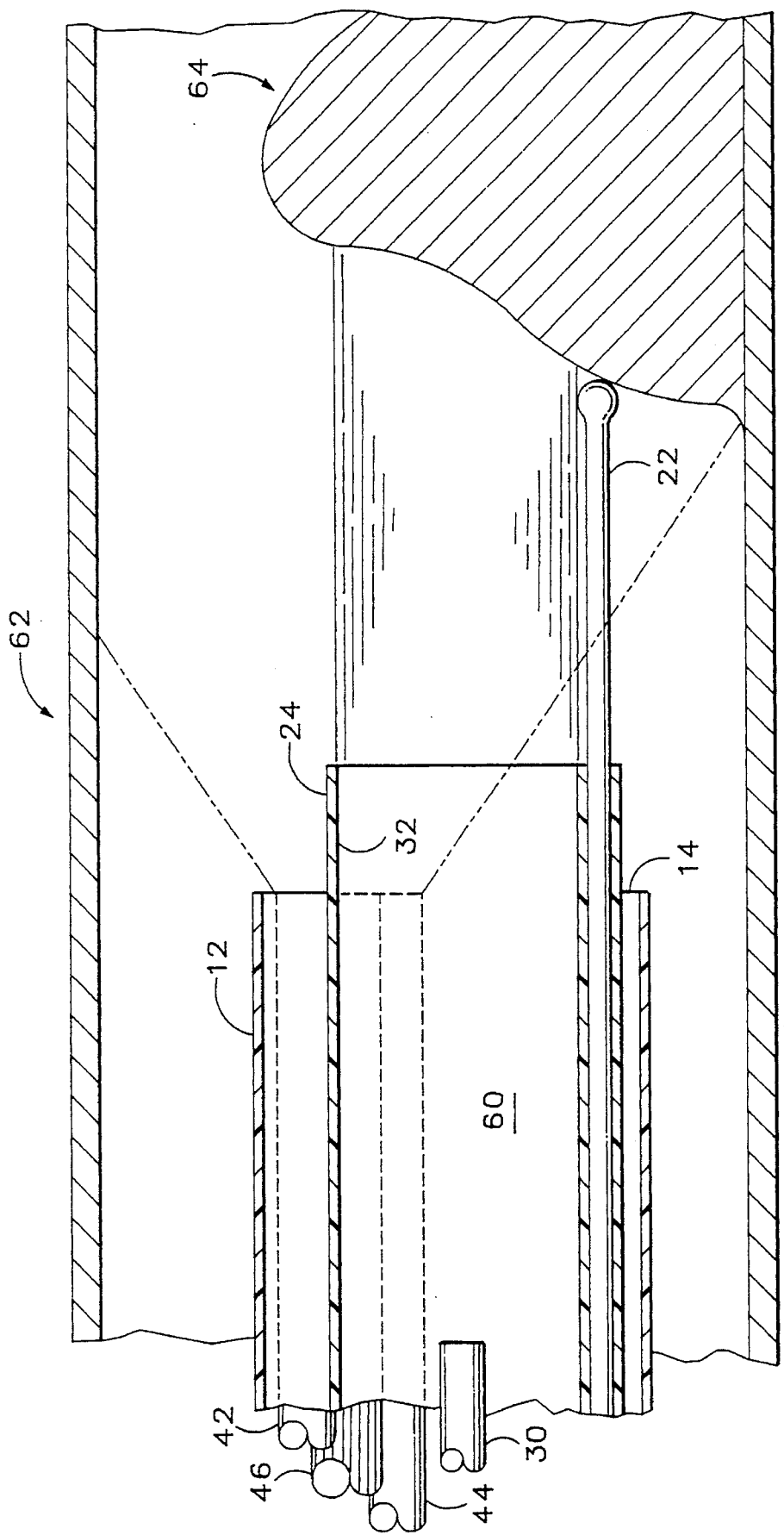
FIG. 3 is a lengthwise sectional view of the distal end portion of the system of FIG. 1 shown in an arterial lumen in proximity to a blood clot.

In the following description of a preferred embodiment of the invention, I now describe a system for locally delivering a pharmacologic agent or active agent in conjunction with delivering laser energy to a site in a body lumen. Those skilled in the art will appreciate that the invention has particular utility in treating obstructions in the cardiovascular system such as atheromatous plaque, an atheroembolus, thrombus, and blood clots. In addition, in its broader aspects, the invention has utility in medically treating tumors, lesions, kidney stones, gall stones, polyps, and the like.

FIG. 1 illustrates the liquid core laser drug delivery system 10 of the present invention, shown in schematic form. System 10 must be capable of delivering an active agent within a body lumen to the site to be treated. In addition, system 10 must be capable of transmitting a pulse of laser energy to the site. The advantages of using a liquid core laser during angioplasty, for example, is discussed by Gregory et al. in the article "Liquid Core Light Guide for Laser Angioplasty", *IEEE Journal of Quantum Electronics*, Vol. 26, No. 12, December 1990.

In general terms, system 10 comprises a tube or catheter 12 having a flexible distal end 14 for insertion into a lumen, an external source 16 of laser energy coupled to optical fiber 30, an external source 18 of light transmissive liquid, and an external source 20 of the active agent. Catheter 12 includes any medical device designed for insertion into a body lumen to permit injection of fluids, to keep the body lumen open, or for any other purpose. The present invention has applicability for use within any body lumen including, among others, an artery, a vein, a ureter, a common bile duct, a trachea, a bronchus, a gastrointestinal tract, a bypass graff, and a graft or prosthesis using gortex, dacron or other synthetic materials, and a stent composed of metal or other materials or combination of materials.

System 10 can also include a guidewire 22 which guides the distal end 14 to the site. As shown in FIG. 2, the catheter 12 encloses conduit 24, having sidewall 32, which is filled with a transparent liquid having a suitable index of refraction. The conduit's sidewall defines a lumenal surface and has either a reflective internal surface (e.g., a metal coating) or suitably low index of refraction compared to the light transmissive liquid to allow internal reflection of light through which the liquid flows. Liquid is introduced at the proximal end of the conduit 24 from the liquid source 18. The liquid is discharged into the conduit 24 by way of a liquid injector pump or manual syringe 26. The liquid is coupled into the conduit 24 using a coupling means 28 such as a Y-adapter.

To practice the invention, I first prepare a dose of the pharmacologic agent which I either add directly to the source 18 or optionally keep the dose ready in syringe 20 or other means of injecting a prescribed volume or amount of the agent into the optical stream. Virtually any concentration of pharmacologic agent in solution can be used depending upon the desired medical effect. For example, in the treatment of intravascular thrombosis urokinase 250–1,000,000 units, streptokinase 250–1,000,000 units, recombinant tissue plasminogen activator 25–150 mg, heparin 2500–10,000 units, hirudin, argotropin, hirulog or other anticoagulants, gene products, enzymes, antiplatelet agents, anti-proliferative agents or combinations thereof can be added to the optical fluid. Other agents that are also deployed to combat thrombosis or its sequelae could also be added to the fluid as long as solution of such agents did not decrease the ability to transmit light through the fluid. The treatment of thrombosis is only one of the many medical uses for this invention.

Next, as illustrated in FIG. 3, I insert catheter 12 into lumen 62 and guide the catheter to the site 64 that I have selected for treatment. By way of example only, the present invention can be used for local delivery of a pharmacologic agent to an atheromatous plaque, an atheroembolus, a thrombus, a blood clot, a lesion, a kidney stone, a gall stone, a tumor, or a polyp.

Preferably, I use a guidewire 22 to position the distal end 14 of catheter 12 adjacent the selected site 64. Once I have positioned the distal end 14 adjacent the site 64, 1 introduce light transmissive liquid 60, containing the dose, at the proximal end of the conduit 24 from the liquid source 18. Liquid discharge means 26 discharges the liquid 60 into the conduit 24. I then direct and couple laser energy from a source of laser energy 16 into the proximal end of optical fiber 30. Fiber 30 launches the laser energy into the liquid 60. The energy passes within the liquid filled conduit 24 toward distal end 14. The proportion of the energy introduced into the liquid 60 that emerges from the distal end 14 of the liquid filled conduit 24 depends upon the dimensions and physical characteristics of the liquid and upon the conduit sidewall 32, and on the extend to which the catheter 12 follows a curving course. Optionally, either before or after I activate the laser energy source, I introduce the active agent in solution from the source of active agent 18 into the stream of flowing liquid 60 by depressing syringe 20.

I select materials for sidewall 32 and for liquid 60 based in part to provide a high degree of internal reflection at the conduit surface. Specifically, sidewall 32 and liquid 60 are each transparent to laser energy which is conducted through the conduit 24 while the index of refraction $N_w$ of side wall 32 is less than the index of refraction of $N_f$ of liquid 60. Further, I select material for sidewall 32 in part to provide structural strength as well as flexibility so that the liquid-filled conduit 24 can be bent through curves of small radius without kinking or substantially distorting the cross sectional geometry of the conduit 24. I prefer to make sidewall 32 out of a fluorinated ethylenepropylene which is available commercially, for example, FEP Teflon® a DuPont product, THV-tetrafloroethylene hexafloropropylene and vanillidine floride, a 3M product, or a coating of suitably low index-of-refraction optical media. If an internal metallized reflective surface coating is used, the sidewall need not be optically transparent.

The light transmissive liquid 60 is injectable, transparent in laser wavelengths, and has a refractive index greater than the refractive index of sidewall 32. Suitable liquids include solutions of sugars such as mannitol, glucose, dextrose, and iodinated contrast media. I prefer a solution having a refractive index of about 1.4. For example, FEP Teflon® has a refractive index of about 1.33, thus, the ratio of refractive indices relative to such solutions is approximately 1.1. A ratio of 1.1 provides for substantially total internal reflection even at fairly steep angles of incidence. I prefer that the surface of sidewall 32 be smooth because if it is not, surface roughness can produce unsatisfactory irregularities in angle of incidence.

The liquid-filled conduit 24 generally has an inside diameter of about 100 to 3000 micrometers. The thickness of the sidewall 121 is generally less than 0.010 inches. A conduit that is 110 cm long, has an interior sidewall of FEP Teflon® and contains a sugar solution or contrast medium, can transmit about 40–60% of the laser energy at 480 nm to the distal end to be launched through a refractive index-matched lens or window into the proximal end from a laser. I prefer to launch laser energy from the optical fiber 30 into the fluid stream at a distance from the tip of catheter 112 to a position ranging about 20 cm withdrawn from the distal end 14. The shorter the distance from the launch point to the distal aspect of the catheter, the higher the percentage transmission of laser energy.

The diameter of catheter 12 is about 0.1–3 mm depending upon the diameter of the body lumen. Some materials that are optically suitable for use as a catheter sidewall are structurally unsuitable or less suitable because they are insufficiently flexible, or they collapse or kink or otherwise are distorted when they are bent through curves of small radius.

The liquid core laser drug delivery system 10 operates generally as follows, with specific reference to its use for ablating and pharmacologically treating arteries or veins occluded by thrombus. Fill conduit 24 with liquid, and then couple a source 18 of liquid to the proximal end of conduit 24. Introduce the liquid-filled conduit 24, distal end first through an opening in the skin and through the wall of a large artery such as the femoral artery. Then direct the catheter toward the selected site, until the distal end 14 is directed toward the occlusion. Then activate the laser energy source 16 to produce laser energy having the desired wavelength and pulse duration and intervals.

Optionally, system 10 can include a laser optical scope, as shown in FIG. 1. The laser optical scope must be capable of performing three functions within the lumen. The first two of these relate to the illumination and imaging of the interior of the lumen to enable the scope's operator to successfully propagate the distal end of the system through the lumen to the site. Accordingly, the output from a source of visible light, such as a Halogen or Xenon lamp 40, is directed to the proximal ends of optical fibers 42 and 44. The other (distal) end of these fibers is housed within the flexible catheter 12 and enable it to be fed through the lumen. A coherent bundle of optical fibers 46 located adjacent to optical fibers 42 and 44 within the catheter 12 receives the image from the illuminated interior of the lumen and transmits it through an excluding means 48 to a viewing port 50 where the image can be monitored by the operator as the flexible catheter 12 is being positioned inside the lumen. Alternatively, the image can be transmitted to a video camera 52 which displays the image on the video monitor 54 for viewing by the operator. A filter must be placed prior to the eyepiece or imaging equipment to filter out the majority of the laser light to prevent injury to the viewer's eye or saturation or damage to a CCD imager.

Embodiments of the invention which include an optical scope allow the operator to monitor the progress of catheter 12 through the lumen via viewing port 50 without interruption or alternatively in monitor 54. Once the distal end has reached the site and is directed toward the target, a further quantity of liquid can be introduced into the catheter from the liquid source 18, causing some liquid to emerge from the distal end of the catheter toward the site. Blood situated between the catheter and the site can interfere with laser ablation of the plaque, because the blood absorbs nearly all wavelengths of laser energy. The liquid passing from the distal end 14 of the catheter 12 displaces blood between the catheter and the site removing this interference. As the emerging liquid displaces the blood, it provides a liquid channel distal to the distal end of the catheter for passage of laser energy to the site, as best seen in FIG. 3. Moreover, the index of refraction of blood is about 1.34, sufficiently low relative to that of the liquid that the blood surrounding the liquid in this channel can form an effective light guide between the distal end of the catheter and the site. In such a temporary liquid-core, the liquid-clad light channel can be effective over distances in the order of about a centimeter for time intervals generally sufficient in usual circumstances to complete the ablation and open the arterial lumen.

Then the laser energy source 16 is activated to produce laser energy having the desired wavelength and pulse duration and intervals. The progress of the laser ablation of the site can be observed through the viewing port 50 or video monitor 54, as the liquid serves not only as a light guide component but also to flush the blood away from the target. When the ablation and drug delivery are completed, I withdraw the liquid-filled catheter from the lumen.

Optionally, I use a guidewire 22 in the above-described procedure, for example, if the walls of the arteries to be traversed by the catheter themselves contain plaque formations that would interfere with the passage of the distal end of the tube during insertion.

Having described and illustrated the principles of the invention in a preferred embodiment thereof, it should be apparent that the invention cain be modified in arrangement and detail without departing from such principles. I claim all modifications and variations coming within the spirit and scope of the following claims.

I claim:

1. A method for contemporaneously applying light energy and locally delivering pharmacologic therapy to a selected site in a body lumen using a liquid core laser catheter, the catheter including a flexible tube having a distal end for insertion into the lumen, a conduit housed within the tube, means for coupling a flow of light transmissive liquid from an external source into the conduit, means for transmitting light energy from a light energy source into the conduit, the conduit having a sidewall capable of reflecting light into the liquid in the conduit so that the liquid guides the light energy through the conduit to the site, the method comprising the steps of:

preparing a dose of pharmacologic agent;

introducing the dose of pharmacologic agent into the light transmissive liquid;

inserting the catheter into the lumen;

directing the catheter to the site;

flowing the light transmissive liquid, containing the pharmacologic agent, through the conduit for discharge at the distal end into the lumen adjacent the site; and delivering light energy through said conduit via the light transmissive liquid to the distal end of the conduit to irradiate the site contemporaneously with discharge of the pharmacologic agent.

2. The method of claim 1 wherein the pharmacologic agent is selected from one or more of the group consisting of urokinase, streptokinase, recombinant tissue plasminogen activator, heparin, hirudin, argotropin, hirulog, anticoagulants, enzymes, anti-platelet agents, anti-proliferative agents, and gene products.

3. The method of claim 1 wherein the light transmissive liquid is injectable and transparent in laser wavelengths.

4. The method of claim 1 wherein the light transmissive liquid comprises a liquid selected from the group consisting of mannitol, glucose, dextrose, and iodinated contrast medium.

5. The method of claim 1 wherein the light energy is laser energy.

6. The method of claim 1 wherein the light energy is incoherent light.

7. The method of claim 1 including selecting materials for use as the conduit and the light transmissive liquid which have relative indices of refraction such that the conduit sidewall is an optically transparent material having an index of refraction less than an index of refraction of the light transmissive liquid so as to be capable of reflecting light into the liquid in the conduit.

8. The method of claim 1 including forming the conduit sidewall with a metallic reflective internal coating for reflecting light into the liquid in the conduit.

9. The method of claim 8 wherein the light transmissive liquid comprises saline solution.

10. The method of claim 1 wherein the lumen is selected from the group consisting of an artery, a vein, a ureter, a common bile duct, a trachea, a bronchus, a gastrointestinal tract, a bypass graft, a stent, and a prothesis or graff composed of synthetic materials.

11. The method of claim 1 wherein the site is selected from the group consisting of an atheromatous plaque, an atheroembolus, a thrombus, a blood clot, a lesion, a kidney stone, a gall stone, a tumor, and a polyp.

12. A method for contemporaneously applying laser energy and locally delivering a flow of pharmacologic agent to a selected site in a body lumen using a liquid core laser angioscope catheter, the catheter including a flexible tube having a distal end for insertion into the lumen, a conduit housed within the tube, means for coupling a flow of light transmissive liquid from an external source into the conduit, means for transmitting visible light from an external source through the tube to illuminate the site, means disposed in the distal end of the tube for imaging the illuminated site and transmitting a visible image thereof through the tube to an external viewing port, means for transmitting laser energy from an energy source into the conduit, the conduit having a sidewall capable of internally reflecting light into the liquid in the conduit so that the liquid waveguides the laser energy through the conduit to the site, the method comprising the steps of:

preparing a solution of the pharmacologic agent;

inserting the catheter into the lumen;

directing the catheter to the site;

transmitting visible light to the site;

flowing the light transmissive liquid through the conduit;

viewing the site through the light transmissive liquid;

transmitting laser energy through the light transmissive liquid flowing through the conduit to treat the site; and introducing a flow of the pharmacologic agent in solution into the conduit for discharge at the distal end into the lumen adjacent the site contemporaneously with the transmission of laser energy to the site.

* * * * *